United States Patent
Chaoui (10) Patent No.: US 12,349,979 B2
(45) Date of Patent: Jul. 8, 2025

(54) USE OF BONY LANDMARKS IN COMPUTERIZED ORTHOPEDIC SURGICAL PLANNING

(71) Applicant: Howmedica Osteonics Corp., Mahwah, NJ (US)

(72) Inventor: Jean Chaoui, Locmaria Plouzané (FR)

(73) Assignee: Howmedica Osteonics Corp., Mahwah, NJ (US)

( * ) Notice: Subject to any disclaimer, the term of this patent is extended or adjusted under 35 U.S.C. 154(b) by 421 days.

(21) Appl. No.: 17/770,887

(22) PCT Filed: Oct. 20, 2020

(86) PCT No.: PCT/US2020/056500
§ 371 (c)(1),
(2) Date: Apr. 21, 2022

(87) PCT Pub. No.: WO2021/086687
PCT Pub. Date: May 6, 2021

(65) Prior Publication Data
US 2022/0387110 A1   Dec. 8, 2022

Related U.S. Application Data

(60) Provisional application No. 62/927,277, filed on Oct. 29, 2019.

(51) Int. Cl.
*A61B 34/10* (2016.01)
*A61F 2/40* (2006.01)

(52) U.S. Cl.
CPC ............. *A61B 34/10* (2016.02); *A61F 2/40* (2013.01); *A61B 2034/108* (2016.02)

(58) Field of Classification Search
CPC . A61B 2034/108; A61B 34/10; A61B 6/5217; A61B 6/505; A61B 5/4576; A61B 5/7267
See application file for complete search history.

(56) References Cited

U.S. PATENT DOCUMENTS 7,542,791 B2   6/2009   Mire et al.
8,214,016 B2   7/2012   Lavallee et al.
(Continued)

FOREIGN PATENT DOCUMENTS

EP   1858430 B1   10/2013
EP   2303192 B1   11/2018
(Continued)

OTHER PUBLICATIONS

Giannotti et al., "Indices of Risk Assessment of Fracture of the Proximal Humerus," Clinical Cases in Mineral and Bone Metabolism, vol. 9, No. 1, Jan.-Apr. 2012, pp. 37-39.
(Continued)

*Primary Examiner* — Samuel S Hanna
(74) *Attorney, Agent, or Firm* — Shumaker & Sieffert, P.A.

(57) ABSTRACT

A computing system generates, based on medical imaging data of bones of a joint of a patient, bony landmark data that characterizes relationships between two or more landmarks on one or more of the bones of the joint of the patient. Additionally, the computing system applies a classifier algorithm that has been trained using training data to select a class associated with the patient from among a plurality of classes. The classifier algorithm takes the bony landmark data of the patient as input.

18 Claims, 3 Drawing Sheets

(56) References Cited

U.S. PATENT DOCUMENTS

| | | |
|---|---|---|
| 8,617,174 B2 | 12/2013 | Axelson, Jr. et al. |
| 8,764,836 B2 | 7/2014 | De Wilde et al. |
| 8,990,052 B2 | 3/2015 | Lavallee et al. |
| 9,301,812 B2 | 4/2016 | Kehres et al. |
| 9,345,548 B2 | 5/2016 | Schoenefeld et al. |
| 9,408,698 B2 | 8/2016 | Miles et al. |
| 9,649,170 B2 | 5/2017 | Park et al. |
| 9,684,768 B2 | 6/2017 | Lavallee et al. |
| 9,717,508 B2 | 8/2017 | Iannotti et al. |
| 9,737,367 B2 | 8/2017 | Steines et al. |
| 9,741,263 B2 | 8/2017 | Iannotti et al. |
| 10,172,715 B2 | 1/2019 | De Wilde et al. |
| 10,537,390 B2 | 1/2020 | Varadarajan et al. |
| 10,922,448 B2 | 2/2021 | McKinnon et al. |
| 11,033,335 B2 | 6/2021 | Zhang |
| 11,071,592 B2 | 7/2021 | McGuan et al. |
| 11,083,525 B2 | 8/2021 | Varadarajan et al. |
| 11,166,764 B2 | 11/2021 | Roh et al. |
| 11,298,188 B2 | 4/2022 | Kehres et al. |
| 11,337,762 B2 | 5/2022 | McKinnon et al. |
| 11,419,680 B2 | 8/2022 | Knotaxis et al. |
| 11,432,931 B2 | 9/2022 | Lang |
| 11,490,965 B2 | 11/2022 | Bischoff et al. |
| 11,490,966 B2 | 11/2022 | Roche et al. |
| 11,622,818 B2 | 4/2023 | Siemionow et al. |
| 11,653,976 B2 | 5/2023 | Bonny et al. |
| 2008/0058613 A1 | 3/2008 | Lang et al. |
| 2018/0233222 A1 | 8/2018 | Daley et al. |
| 2018/0247020 A1 | 8/2018 | Itu et al. |
| 2018/0325526 A1 | 11/2018 | Haddad |
| 2019/0029757 A1 | 1/2019 | Roh et al. |
| 2019/0090952 A1 | 3/2019 | Bonny et al. |
| 2019/0142519 A1 | 5/2019 | Siemionow et al. |
| 2020/0113632 A1 | 4/2020 | Varadarajan et al. |
| 2020/0281728 A1 | 9/2020 | Kulper et al. |
| 2021/0030477 A1 | 2/2021 | Zuhars et al. |
| 2021/0128179 A1 | 5/2021 | Dupuis et al. |
| 2021/0196290 A1 | 7/2021 | Iannotti et al. |
| 2021/0307833 A1 | 10/2021 | Farley et al. |
| 2021/0330389 A1 | 10/2021 | Varadarajan et al. |
| 2022/0054197 A1* | 2/2022 | Plessers ................. G16H 50/50 |
| 2022/0125515 A1 | 4/2022 | McGuan et al. |
| 2022/0183757 A1 | 6/2022 | Caldera et al. |
| 2022/0249168 A1 | 8/2022 | Besier et al. |
| 2022/0346968 A1 | 11/2022 | Pettersson et al. |
| 2023/0085093 A1 | 3/2023 | Chaoui et al. |

FOREIGN PATENT DOCUMENTS

| | | |
|---|---|---|
| EP | 3481318 B1 | 9/2022 |
| WO | 2022169678 A1 | 8/2022 |

OTHER PUBLICATIONS

Tingart et al., "The cortical thickness of the proximal humeral diaphysis predicts bone mineral density of the proximal humerus," Journal of Bone and Joint Surgery, vol. 85-B, No. 4, May 2023, pp. 611-617.

Blonna et al., "Predominance of the critical shoulder angel in the pathogenesis of degenerative diseases of the shoulder", Journal of Shoulder and Elbow Surgery, vol. 25, No. 8, Feb. 15, 2016, Pages pp. 1328-1336.

International Preliminary Report on Patentability from International Application No. PCT/US2020/056500, dated May 12, 2022, 11 pp.

International Search Report and Written Opinion of International Application No. PCT/US2020/056500, dated Mar. 31, 2021, 15 pp.

Moor et al., "Relationship of individual scapular anatomy and degenerative rotator cuff tears", Journal of Shoulder and Elbow Surgery, vol. 23, No. 4, Jan. 28, 2014, Pages pp. 536-541.

\* cited by examiner

USE OF BONY LANDMARKS IN COMPUTERIZED ORTHOPEDIC SURGICAL PLANNING

This application is a national stage application under 35 U.S.C. § 371 of PCT Application No. PCT/US2020/056500, filed Oct. 20, 2020, which claims the benefit of U.S. Provisional Application No. 62/927,277, filed Oct. 29, 2019.

BACKGROUND

Planning of orthopedic shoulder surgeries is a complicated task. This task is further complicated because surgeons may have difficulty determining the qualities and properties of the soft tissue surrounding the bones of the shoulder joint. For example, it may be difficult for a surgeon to understand, based on x-ray images, whether the patient has a rotator cuff tear because a rotator cuff tear is a condition of the muscles surrounding the shoulder joint and not a condition of the bones of the shoulder joint. Similar considerations apply with respect to determining whether the patient has a rotator cuff tear. However, whether the patient has a rotator cuff tear may be key factors in determining whether to perform an anatomic total shoulder arthroplasty or a reverse total shoulder arthroplasty.

SUMMARY

This disclosure describes example techniques for automated planning of orthopedic shoulder surgeries. The techniques of this disclosure may improve reliability and accuracy of certain aspects of the planning process for orthopedic shoulder surgeries. As described herein, a computing system may generate, based on medical imaging data of bones of a joint of a patient, bony landmark data that characterizes relationships between two or more landmarks on one or more of the bones associated with the joint of the patient. The computing system may then apply a classifier algorithm that has been trained using training data to select a class associated with the patient from among a plurality of classes. The classifier algorithm takes the bony landmark data of the patient as input. The classifier algorithm is a type of machine learning algorithm, such as a neural network algorithm, a support vector machine algorithm, or a random forest algorithm. The bony landmark data may serve as a substitute for direct information about the soft tissue surrounding the shoulder joint, and therefore may be used as a proxy for classifying the patient.

In one example, this disclosure describes a method comprising: generating, by a surgical assistance system and based on medical imaging data of bones of a joint of a patient, bony landmark data that characterizes one or more relationships between two or more landmarks of one or more bones of the bones of the joint of the patient; and applying, by the surgical assistance system, a classifier algorithm that has been trained using training data to select a class associated with the patient from among a plurality of classes, wherein the classifier algorithm takes the bony landmark data of the patient as input. In another example, this disclosure describes a computing system comprising: a memory configured to store medical imaging data; and processing circuitry configured to perform this method. In another example, this disclosure describes a computing system comprising: means for storing medical imaging data; and means for performing this method. In another example, this disclosure describes a computer-readable data storage medium having instructions stored thereon that, when executed, cause a computing system to perform this method.

The details of various examples of the disclosure are set forth in the accompanying drawings and the description below. Various features, objects, and advantages will be apparent from the description, drawings, and claims.

DETAILED DESCRIPTION

As briefly discussed above, planning of orthopedic shoulder surgeries is a complicated task. Thus, while orthopedic shoulder surgeries are relatively common procedures, the complexities of planning orthopedic shoulder surgeries tend to limit the number of surgeons who routinely perform orthopedic shoulder repair surgeries. This increases the cost of performing orthopedic shoulder surgeries. Thus, it may be desirable to implement computerized tools to help surgeons plan orthopedic shoulder surgeries. Such computerized tools may use data regarding a patient to recommend specific surgical options to the surgeon.

As mentioned above, understanding the properties and qualities of the soft tissue surrounding a patient's shoulder joint may be useful for planning orthopedic shoulder repair surgeries. For instance, it may be desirable to obtain information such as whether the patient has a rotator cuff tear, a degree of fatty infiltration into the rotator cuff muscles, and other information regarding the soft tissue surrounding a patient's shoulder joint. Thus, it may be desirable to use information regarding the soft tissue surrounding the patient's shoulder joint in computerized tools that help surgeons plan orthopedic shoulder surgeries.

A surgical assistance system may be able to determine much of the desired information regarding the soft tissue surrounding the patient's shoulder joint through the application of image segmentation techniques to computed tomography (CT) scans of the patient's shoulder. However, application of image segmentation techniques to CT scans is a computationally intensive task and one that is prone to error. For instance, image segmentation to analyze soft tissue may require complex artificial neural networks. The task of image segmentation is made even more difficult because soft tissue is more difficult to identify than bone in x-ray images. Alternatively, images of the soft tissue may be generated using Magnetic Resonance Imaging (MRI), but MRI is considerably more expensive than x-ray imaging and is available in fewer places. Regardless of the imaging technology used, training a surgical assistance system to perform the image segmentation techniques may require a large amount of training data, which imposes significant computational burdens on computing systems.

The techniques of this disclosure may address one or more of these issues. As described herein, a surgical assistance system may generate, based on medical imaging data of bones of a joint of a patient, bony landmark data that characterizes relationships between two or more landmarks on one or more of the bones of the joint of the patient. For example, a spatial relationship between landmarks on different bones may represent soft tissue characteristics of muscles or other connective tissue associated with those different bones. The surgical assistance system may apply a classifier algorithm that has been trained using training data to select a class associated with the patient from among a plurality of classes. The classifier algorithm takes the bony landmark data of the patient as input. The bony landmark data may thus serve as a proxy for data regarding the soft tissue surrounding the patient's shoulder joint.

Because the surgical assistance system is generating the bony landmark data based on imaging data of the bones, as opposed to the soft tissue itself, it may not be necessary to perform more expensive CT or MRI scans of the patient in order to obtain the needed information regarding the soft tissue. Moreover, it may be computationally more efficient to analyze medical imaging data of the bones than the soft tissue because landmarks on the bones are typically more prominent, and less susceptible to imaging artifacts. Moreover, computing tasks for segmenting different types of soft tissue may be avoided. These factors may reduce the demands on the computational resources of the surgical assistance system, potentially increasing processing speed and/or enabling the surgical assistance system to be implemented using less complex hardware.

Figure 1:
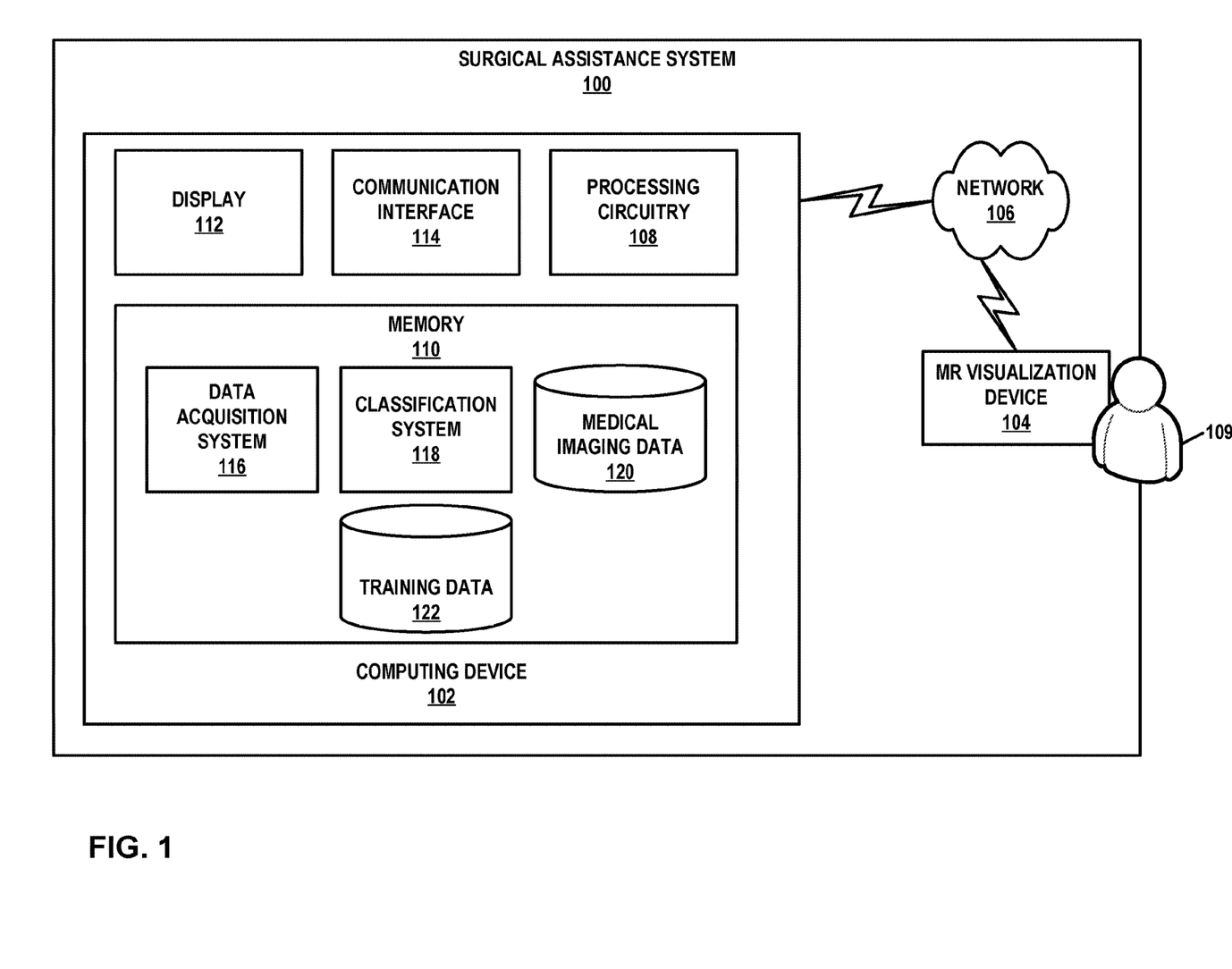
FIG. 1 is a block diagram illustrating an example surgical assistance system that may implement the techniques of this disclosure.

FIG. 1 is a block diagram illustrating an example surgical assistance system 100 that may be used to implement one or more techniques of this disclosure. Surgical assistance system 100 is an example of a computing system that may implement the techniques of this disclosure. In the example of FIG. 1, surgical assistance system 100 includes a computing device 102, a MR visualization device 104, and a network 106. In other examples, surgical assistance system 100 may include more or fewer devices or systems. For instance, in some examples, tasks performed by computing device 102 may be performed by MR visualization device 104. In other examples, tasks described in this disclosure as being performed by computing device 102 may be performed by a system of multiple computing devices. Furthermore, in some examples, surgical assistance system 100 may include multiple MR visualization devices or may include no MR visualization devices. In some examples, surgical assistance system 100 does not include network 106.

Computing device 102 of surgical assistance system 100 may include various types of computing devices, such as server computers, personal computers, smartphones, laptop computers, and other types of computing devices. In the example of FIG. 1, computing device 102 includes processing circuitry 108, memory 110, display 112, and a communication interface 114. Display 112 is optional, such as in examples where computing device 102 comprises a server computer.

Examples of processing circuitry 108 include one or more microprocessors, digital signal processors (DSPs), application specific integrated circuits (ASICs), field programmable gate arrays (FPGAs), hardware, or any combinations thereof. In general, processing circuitry 108 may be implemented as fixed-function circuits, programmable circuits, or a combination thereof. Fixed-function circuits refer to circuits that provide particular functionality and are preset on the operations that can be performed. Programmable circuits refer to circuits that can programmed to perform various tasks and provide flexible functionality in the operations that can be performed. For instance, programmable circuits may execute software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable. In some examples, the one or more of the units may be distinct circuit blocks (fixed-function or programmable), and in some examples, the one or more units may be integrated circuits.

Processing circuitry 108 may include arithmetic logic units (ALUs), elementary function units (EFUs), digital circuits, analog circuits, and/or programmable cores, formed from programmable circuits. In examples where the operations of processing circuitry 108 are performed using software executed by the programmable circuits, memory 110 may store the object code of the software that processing circuitry 108 receives and executes, or another memory within processing circuitry 108 (not shown) may store such instructions. Examples of the software include software designed for surgical planning. Processing circuitry 108 may perform the actions ascribed in this disclosure to surgical assistance system 100.

In the example of FIG. 1, memory 110 stores instructions for a data acquisition system 116 and a classification system 118. Execution of the instructions for data acquisition system 116 by processing circuitry 108 may cause computing device 102 to provide the functionality ascribed in this disclosure to data acquisition system 116. Execution of the instructions for classification system 118 by processing circuitry 108 may cause computing device 102 to provide the functionality ascribed in this disclosure to classification system 118.

Memory 110 may store various types of data used by processing circuitry 108. For example, memory 110 may store data describing 3D models of various anatomical structures, including morbid and predicted premorbid anatomical structures. For instance, in one specific example, memory 110 may store data describing a 3D model of a humerus of a patient, imaging data, and other types of data.

Memory 110 may be formed by any of a variety of memory devices, such as dynamic random access memory (DRAM), including synchronous DRAM (SDRAM), magnetoresistive RAM (MRAM), resistive RAM (RRAM), or other types of memory devices. Examples of display 112 may include a liquid crystal display (LCD), a plasma display, an organic light emitting diode (OLED) display, or another type of display device.

Communication interface 114 of computing device 102 allows computing device 102 to output data and instructions to and receive data and instructions from MR visualization device 104 via network 106. Communication interface 114 may be hardware circuitry that enables computing device 102 to communicate (e.g., wirelessly or using wires) to other computing systems and devices, such as MR visualization device 104. Network 106 may include various types of communication networks including one or more wide-area networks, such as the Internet, local area networks, and so on. In some examples, network 106 may include wired and/or wireless communication links.

MR visualization device 104 may use various visualization techniques to display MR visualizations to a user 109, such as a surgeon, nurse, technician, or other type of user. A MR visualization may comprise one or more virtual objects that are viewable by a user at the same time as real-world objects. Thus, what the user sees is a mixture of real and virtual objects. It is noted that user 109 does not form part of surgical assistance system 100.

MR visualization device 104 may comprise various types of devices for presenting MR visualizations. For instance, in some examples, MR visualization device 104 may be a Microsoft HOLOLENS™ headset, available from Microsoft Corporation, of Redmond, Washington, USA, or a similar device, such as, for example, a similar MR visualization device that includes waveguides. The HOLOLENS™ device can be used to present 3D virtual objects via holographic lenses, or waveguides, while permitting a user to view actual objects in a real-world scene, i.e., in a real-world environment, through the holographic lenses. In some examples, MR visualization device 104 may be a holographic projector, head-mounted smartphone, special-purpose MR visualization device, or other type of device for presenting MR visualizations. In some examples, MR visualization device 104 includes a head-mounted unit and a backpack unit. In other examples, all functionality of MR visualization device 104 is performed in a head-mounted unit.

MR visualization device 104 may use visualization tools that are available to utilize patient image data to generate 3D models of bone contours to facilitate preoperative planning for joint repairs and replacements. These tools allow surgeons to design and/or select surgical guides and implant components that closely match the patient's anatomy. These tools can improve surgical outcomes by customizing a surgical plan for each patient. An example of such a visualization tool for joint repair surgeries is the BLUEPRINT™ system available from Wright Medical Technology, Inc. The BLUEPRINT™ system provides the surgeon with two-dimensional planar views of the joint-repair region as well as a three-dimensional virtual model of the joint-repair region. The surgeon can use the BLUEPRINT™ system to select, design or modify appropriate orthopedic prostheses, determine how best to position and orient the orthopedic prostheses, how to shape the surface of bones to receive the orthopedic prostheses, and how design, select or modify surgical guide tool(s) or instruments to carry out a surgical plan. The information generated by the BLUEPRINT™ system may be compiled in a preoperative surgical plan for the patient that is stored in a database at an appropriate location (e.g., on a server in a wide area network, a local area network, or a global network) where it can be accessed by the surgeon or other care provider, including before and during the actual surgery.

Discussion in this disclosure of actions performed by surgical assistance system 100 may be performed by one or more computing devices (e.g., computing device 102) of surgical assistance system 100, MR visualization device 104, or a combination of the one or more computing devices and MR visualization device 104.

User 118 may use surgical assistance system 100 during a preoperative phase of an orthopedic surgery and an intraoperative phase of the orthopedic surgery. The preoperative phase of the orthopedic surgery may occur before performance of the orthopedic surgery. The orthopedic surgery may be an original orthopedic surgery or an orthopedic revision surgery.

During the preoperative phase of an orthopedic shoulder surgery, data acquisition system 116 of surgical assistance system 100 may obtain, and memory 110 may store, medical imaging data 120 of bones of a shoulder joint of a patient. In some examples, medical imaging data 120 includes x-ray images of the shoulder joint of the patient. In some examples, medical imaging data 120 includes CT models of the shoulder joint of the patient. In some examples, data acquisition system 116 may obtain medical imaging data 120 directly from a medical imaging device, such as a digital x-ray machine. In some examples, data acquisition system 116 may obtain medical imaging data 120 from a remote data source, such as an electronic medical records data store. Although x-ray imaging is described herein, any type of imaging modality in which bones can be detected may be used to obtain medical imaging data 120.

Furthermore, data acquisition system 116 may generate, based on medical imaging data 120 of the bones of the shoulder joint of a patient, bony landmark data that characterizes relationships between two or more landmarks on one or more of the bones of the joint of the patient. In various examples, data acquisition system 116 may generate various types of bony landmark data.

Figure 2:
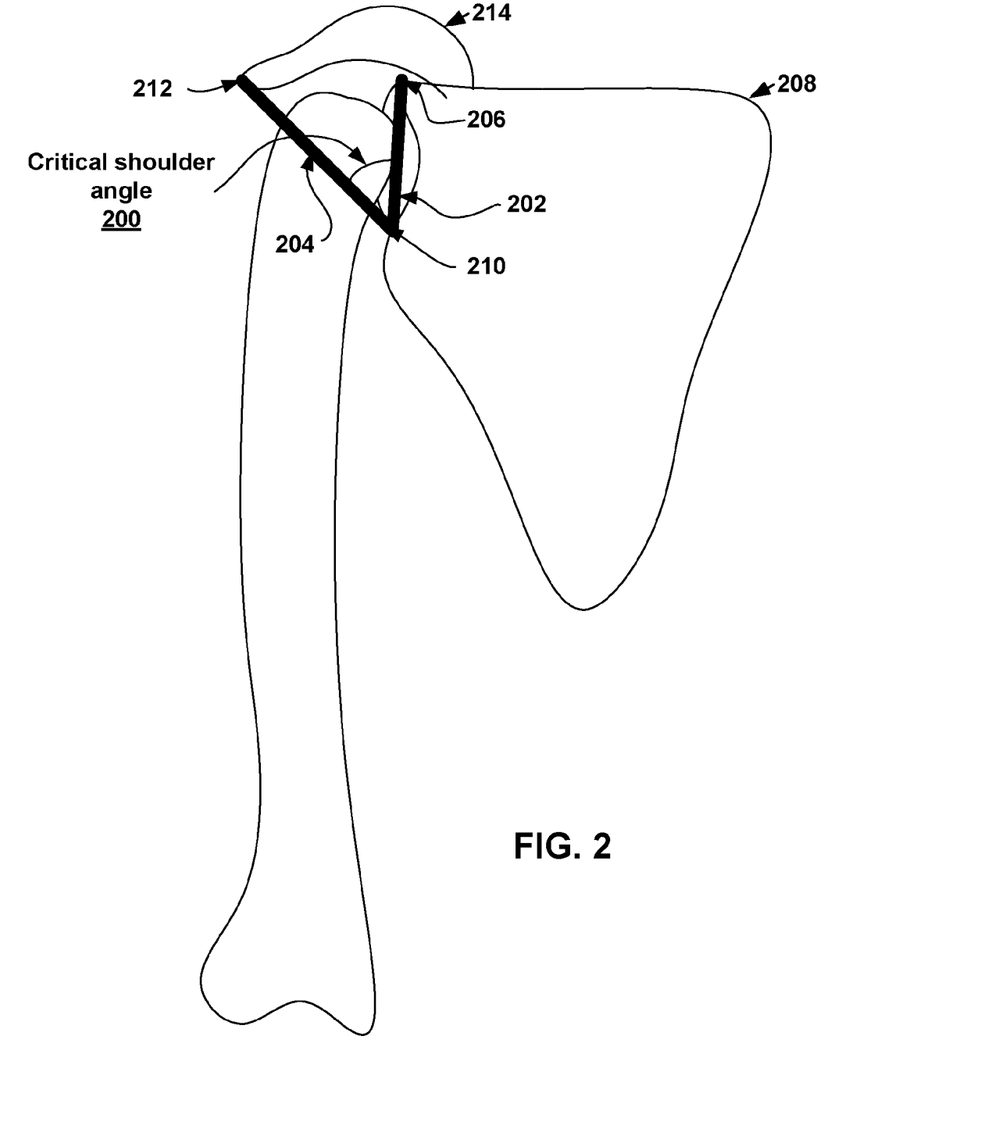
FIG. 2 is a conceptual diagram illustrating an example critical shoulder angle.

For example, data acquisition system 116 may determine a critical shoulder angle (CSA) of the patient and include data indicating the CSA of the patient into the bony landmark data. FIG. 2 is a conceptual diagram illustrating an example critical shoulder angle. The CSA of the patient is an angle 200 between a first line 202 and a second line 204. The first line 202 is a line between a most superior point 206 on a border of a glenoid cavity of a scapula 208 of the patient and a most inferior point 210 on the border of the glenoid cavity of the scapula 208 of the patient. The second line 204 is a line between the most inferior point 210 on the border of the glenoid cavity of the scapula 208 of the patient and a most lateral point 212 of an acromion 214 of the scapula 208 of the patient. In general, smaller CSAs are correlated with increased glenoid wear, which is a sign of cuff tear arthropathy.

In other examples, surgical assistance system 100 may determine other relationships between landmarks of one or more bones, such as:

A distance from a humeral head center to a glenoid center.

A distance from the acromion to the humeral head.

A scapula critical shoulder sagittal angle (i.e., an angle between the lines mentioned above for the CSA, as the lines would be seen from a sagittal plane of the patient).

A glenoid coracoid process angle (i.e., an angle between (1) a line from a tip of the coracoid process to a most inferior point on the border of the glenoid cavity of the scapula, and (2) a line from the most inferior point on the border of the glenoid cavity of the scapula to a most superior point on the border of the glenoid cavity of the scapula).

An infraglenoid tubrical angle (i.e., an angle between (1) a line extending from a most inferior point on the border of the glenoid cavity to a greater tuberosity of the humerus, and (2) a line extending from a most superior point on the border of the glenoid cavity to the most inferior point on the border of the glenoid cavity).

A scapula acromion index (i.e., the ratio between the distance from the plane of the glenoid cavity to the lateral edge of the acromion and the distance from the plane of the glenoid cavity to the lateral edge of the humeral head).

A humerus orientation (i.e., a value indicating an angle between (1) a line orthogonal to the center of the glenoid, and (2) a line orthogonal to the center of the humeral head, as viewed from directly superior to the patient).

A humerus direction (i.e., the polar angle between the projection of the glenohumeral axis and the anteroposterior axis of the glenoid).

A measure of humerus subluxation (i.e., the ratio of the posterior portion of the humeral head with regard to the scapular plane).

A humeral head best fit sphere (i.e., a measure (e.g., a root mean square) of conformance of the humeral head to a sphere).

Data acquisition system 116 may generate bony landmark data that includes any one or more of the above relationships between bony landmarks. After generating the bony landmark data, classification system 118 of surgical assistance system 100 may apply a classifier algorithm that has been trained using training data 122 to select a class associated with the patient from among a plurality of classes. The classifier algorithm takes the bony landmark data of the patient as input. As shown in the example of FIG. 1, memory 110 may store training data 122. In other examples, other computing devices may store the training data.

Different examples of this disclosure may apply to different pluralities of classes. For instance, in some examples, the plurality of different classes is a plurality of different surgeries for the patient (e.g., anatomic total shoulder arthroplasty, reverse total shoulder arthroplasty, hemispheric shoulder arthroplasty, etc.). In some examples, the classes correspond to different pathologies. For instance, in an example where the classes correspond to different pathologies, the pathologies may include cuff tear arthropathy, massive rotator cuff tear, osteonecrosis, rheumatoid arthritis, instability, post traumatic arthritis, primary glenohumeral osteoarthritis, and so on.

In different examples, classification system 118 may implement the classifier algorithm in any of one or more ways. For instance, in some examples, the classifier algorithm may be implemented as one or more neural networks. In such examples, the artificial neural network may include an input layer, an output layer, and one or more hidden layers between the input layer and the output layer. Different types of the bony landmark data may correspond to different artificial neurons of the input layer of an artificial neural network. Furthermore, different artificial neurons of the output layer of the artificial neural network may correspond to different classes in the plurality of classes. For ease of explanation, this disclosure assumes that classification system 118 trains the classifier algorithm. However, in other examples, systems separate from classification system 118 and/or separate from surgical assistance system 100 may train the classifier algorithm.

In examples where the classification algorithm is implemented using an artificial neural network, classification system 118 may train the artificial neural network using training data 122. Training data 122 may include patient training data for a plurality of patients. The training data for a patient may specify patient-specific values for the plurality of physical characteristics. Additionally, the training data for the patient may specify an index of humeral prosthesis implanted in the patient. To train the artificial neural network using a training data set for a patient, classification system 118 may apply a forward pass through the artificial neural network to generate output data indicating an index of a recommended humeral prosthesis. Classification system 118 may then compare the index of the recommended humeral prosthesis to the index of the humeral prosthesis indicated by the training data for the patient. Based on this comparison, classification system 118 may use a backpropagation algorithm to update weight values of artificial neurons in the artificial neural network.

In examples where the plurality of classes includes only two classes, classification system 118 may implement the classifier algorithm using a support vector machine (SVM) algorithm. In this example, the SVM algorithm may be trained with training data 122. When the classifier algorithm is implemented using an SVM algorithm, training data 122 includes a set of samples. Each sample of training data 122 includes an input vector and a target classification. The input vector includes a set of features. The features in the input vector may include bony landmark data for a specific patient, and in some examples, may also include other types of data regarding the specific patient. The target classification is a pre-determined classification associated with the specific patient.

In examples where classification system 118 implements an SVM algorithm, classification system 118 may determine a set of weights w based on training data 122. The set of weights w includes a weight for each feature of the input vector. Furthermore, classification system 118 may determine whether an input vector belongs to a first classification or a second classification, and hence, whether a patient associated with the input vector is associated with the first classification or the second classification, by applying the following formula:

$$\hat{y} = \begin{cases} 0 \text{ if } w^T \cdot x + b < 0 \\ 1 \text{ if } w^T \cdot x + b \geq 0 \end{cases}$$

In the equation above, x denotes the input vector, b denotes a bias term, and ŷ is an index of the class.

Furthermore, in examples where classification system 118 implements an SVM algorithm, classification system 118 may determine the weights w and the bias term b using linear SVM classification or nonlinear SVM classification. Training an SVM classifier entails determining values of w and b that maximize a margin between two lines (i.e., support vectors) that are parallel to a linear decision boundary while avoiding or limiting margin violations (i.e., input vectors that are between the support vectors). In some examples, classification system 118 may use a stochastic gradient descent algorithm, a sequential minimal optimization algorithm, or another algorithm to determine the values of w and b.

In some examples, to use the sequential minimal optimization algorithm, classification system 118 may solve the quadratic programming problem expressed by:

$$\max_\alpha \sum_{i=1}^n \alpha_i - \frac{1}{2} \sum_{i=1}^n \sum_{j=1}^n y_i y_j K(x_i, x_j) \alpha_i \alpha_j,$$

subject to:

$$0 \leq \alpha_i \leq C, \text{ for } i = 1, 2, \ldots, n$$

and $$\sum_{i=1}^n y_i \alpha_i = 0$$

In the equations above, n indicates a number of samples in the dataset, $y_i$ and $y_j$ indicate target classifications of the samples, $x_i$ and $x_j$ indicate input vectors of the samples, $\alpha_i$ and $\alpha_j$ are Lagrange multipliers, $K(x_i, x_j)$ is a kernel function, and C is a SVM hyperparameter. Classification system 118 may use various kernel functions as $K(x_i, x_j)$, such as a linear kernel function, a polynomial kernel function, a Gaussian Radial Basis Function (RBF) kernel function, a sigmoid kernel function, or another type of kernel function.

To solve the quadratic programming problem expressed above, classification system 118 may find a Lagrange multiplier $\alpha_1$ that violates the Karush-Kuhn-Tucker (KKT) conditions for the optimization problem. Classification system 118 may then determine a second Lagrange multiplier $\alpha_2$ and optimize the pair ($\alpha_1$, $\alpha_2$). Classification system 118 may repeat these steps until convergence. When the Lagrange multipliers satisfy the KKT conditions within a tolerance (e.g., a user-defined tolerance), the sequential minimal optimization problem is solved. Classification system 118 may determine the set of weights w and the bias term b as:

$$w = \sum_{i=1}^{n} \alpha_i y_i x_i$$

and $$b = w \cdot x_i - y_i$$

In another example, classification system 118 may implement the classifier algorithm using a random forest algorithm. In this example, classification system 118 may generate a plurality of decision trees using randomly selected samples from training data 122. In other words, for each decision tree in the plurality of decision trees, classification system 118 may generate a tree-specific training dataset that is a subset of the samples in training data 122. In some examples, classification system 118 may use bagging or pasting to select the samples in the tree-specific training datasets for the plurality of decision trees. In examples where the classifier algorithm is implemented using a random forest algorithm, each sample of training data 122 includes an input vector and a target classification. The input vector includes a set of features. The features in the input vector may include bony landmark data for a specific patient, and in some examples, may also include other types of data regarding the specific patient. The target classification is a pre-determined classification associated with the specific patient.

Furthermore, in examples where the classifier algorithm is implemented using a random forest algorithm, each of the decision trees outputs a proposed classification associated with the patient. Classification system 118 may then select one of the proposed classifications as the classification associated with the patient. For example, classification system 118 may use a voting system in which classification system 118 selects, as the classification associated with the patient, a most common one of the proposed classifications.

In examples where the classifier algorithm is implemented using a random forest algorithm, classification system 118 may generate the decision trees using one or more of a variety of decision tree training algorithms. For instance, in some examples, classification system 118 generates the decision tress using a Classification and Regression Tree (CART) algorithm. To perform the CART algorithm, classification system 118 may split the tree-specific training data subset into two subsets using a single feature k and a threshold $t_k$. To select feature k and threshold $t_k$, classification system 118 may search for a pair (k, $t_k$) that produces the "purest" subsets of the tree-specific training data set. A subset is considered "pure" if all of the target classifications in the subset are the same. Example measures for determining the purity of a subset include a Gini impurity measure, an entropy impurity measure, and so on. The following equation is an example cost function that surgical assistance system 100 may use to generate cost values that surgical assistance system 100 may use for comparing combinations of pairs (k, $t_k$).

$$J(k_i, t_k) = \frac{m_{left}}{m} G_{left} + \frac{m_{right}}{m} G_{right}$$

In the equation above, $G_{left/right}$ is a measure of the impurity of the left/right subset, and $m_{left/right}$ is a number of instances in the left/right subset. The "left" and "right" subsets are so named because they may correspond to left and right branches of a decision tree.

In the CART algorithm, after selecting a pair (k, $t_k$) that splits the tree-specific training data subset into two subsets, classification system 118 may further divide these two subsets in the same manner as described above. Classification system 118 may continue recursively dividing subsets in this manner using a maximum depth is reached or surgical assistance system 100 is unable to determine any combination of features and thresholds that reduce impurity within a subset.

In addition to accepting bony landmark data as input, the classifier algorithm implemented by classification system 118 may accept other types of data as input. For instance, in some examples, the classifier algorithm may accept one or more bone density metrics of a bone of the joint as input. In one such example, data acquisition system 116 may partition a region of the bone into blocks and the bone density metrics include a value indicating an average of Hounsfield units for the blocks that exceed a threshold. For instance, data acquisition system 116 may partition a region at a diaphysis of the humeral bone into a first set of blocks and may partition a region at a metaphysis of the humeral bone into a second set of blocks. Data acquisition system 116 may use landmarks like greater and lesser tuberosities to define the surgical neck, use deltoid proximal and lateral insertions, and or use the cylindrical shape of the diaphysis to determine locations of the metaphysis and diaphysis. In some examples, data acquisition system 116 may also use statistical shape modeling with anatomic landmarks and pre-labeled regions, and may match the statistical shape model to the patient bone and match the corresponding regions. In some examples, data acquisition system 116 may use average distances described in the medical literature to determine locations of the diaphysis and metaphysis.

The plurality of physical characteristics of the humeral bone includes (1) an average of Hounsfield units of a first set of blocks that exceed a first threshold, (2) an average of Hounsfield units of the second set of blocks that exceed a second threshold, and (3) an average of Hounsfield units of the first set of blocks that exceed a third threshold different from the first threshold. The first, second, and third thresholds may have various values in different examples. For instance, in one example, the first threshold is equal to 400, the second threshold is equal to 500, and the third threshold is equal to 700. In other examples, the first, second, or third thresholds may have different values, such as 400, 500, 600, 700, 800, 900, 1000, 1100, and so on. In this example, the region may be limited to the cortical bone, or limited to cancellous bone, or may include bone cortical or cancellous bone.

In this example, the first region may be defined as a part of the humerus between a first fixed distance and a second fixed distance from a proximal tip of the greater tuberosity of the humerus. For instance, the first fixed distance may be 8 centimeters and the second fixed distance may be 10 centimeters. In other examples, other fixed distances are possible. Furthermore, in some other examples, the distances are not fixed, but instead may be scaled based on overall height of the patient or an overall length of the humerus.

In this example, data acquisition system 116 may obtain data generated by performing a dual-energy x-ray absorptiometry (DXA) scan of the patient's humerus. In other examples, data acquisition system 116 may obtain data generated by performing a quantitative computed tomography (QCT) scan of the patient's humerus. Data acquisition system 116 may then analyze the obtained data to determine the Hounsfield units of the blocks in the regions of the diaphysis and metaphysis of the humerus.

In other examples, data acquisition system 116 may obtain patient-specific values for other physical characteristics of the humeral bone. For instance, data acquisition system 116 may obtain patient-specific values for one or more Giannotti measurements. A Giannotti measurement is a ratio between a thickness of the cortical bone of the humerus and a total diameter of the humeral diaphysis at a transverse plane passing through the humeral diaphysis. In other words, where the bone is a humerus, the one or more bone density metrics may include a value defined as (x−z)/z, wherein x is an inner diameter of the humerus on a plane located a specific distance inferior to a greater tuberosity of the humerus and z is an outer diameter of the humerus on the plane.

Different Giannotti measurements correspond to different thresholds used to create different binary mask of the bone. In other words, different Giannotti measurements may be generated when only considering parts of the bone having densities above the corresponding threshold. For example, different Giannotti measurements may be generated using thresholds of 900 Hounsfield Units (HU), 1000 HU, or 1100 HU. After applying the binary mask, data acquisition system 116 may measure the thickness of the cortical and the other parameters. Data acquisition system 116 may obtain the Giannotti measurements based on radiographs, CT scans, or other types of medical imaging data 120.

In another example, data acquisition system 116 may obtain patient-specific values for one or more Tingart measurements. A Tingart measurement is a mean of a first value, a second value, a third value, and a fourth value. The first value is the lateral cortical thicknesses of the humeral diaphysis at a first level. The second value is the medial cortical thickness of the humeral diaphysis at the first level. The third value is the lateral cortical thickness of the humeral diaphysis at a second level. The fourth value is the medial cortical thicknesses of the humeral diaphysis at the second level. The first level is at a location on the humeral diaphysis where endosteal borders of the lateral and medial cortices of the humerus are first parallel to each other, as determined from the proximal tip of the humerus. The second level is defined as 20 mm distal from the first level. Data acquisition system 116 may obtain the Tingart measurements based on radiographs. Similar to Giannotti measurements, data acquisition system 116 may obtain Tingart measurements using different thresholds used to create different binary masks of the bone.

In some examples, the classifier algorithm implemented by classification system 118 takes biomechanical model data as input. The biomechanical model data characterizes a biomechanical model of the joint of the patient. For instance, the biomechanical model data may include data indicating at least one of: static stress of muscles on the bones of the joint, static stress of an orthopedic prosthesis on one or more of the bones of the joint, static stress of two orthopedic prostheses of the joint on each other, dynamic stress of muscles on the bones of the joint, dynamic stress of an orthopedic prosthesis on one or more of the bones of the joint, and dynamic stress of two orthopedic prostheses of the joint on each other. Data acquisition system 116 may obtain the biomechanical model based on data received as input by a user. The biomechanical model may include a skeletal model, a musculature model, a musculoskeletal model, a kinematics model, a dynamics model, a joint boundary model, and/or a topological model. However, this disclosure uses biomechanical model as a general term to represent all of them. In addition, classification system 118 may classify these biomechanical models as open-loop chains with different degrees of freedom, closed-loop chains or musculoskeletal models.

Figure 3:
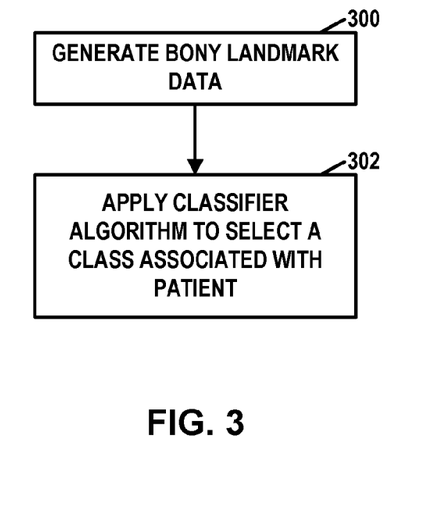
FIG. 3 is a flowchart illustrating an example operation of the surgical assistance system, in accordance with one or more aspects of this disclosure.

FIG. 3 is a flowchart illustrating an example operation of surgical assistance system 100, in accordance with one or more aspects of this disclosure. In the example of FIG. 3, surgical assistance system 100 (e.g., data acquisition system 116 of surgical assistance system 100) may generate, based on medical imaging data 120 of bones of a joint of a patient, bony landmark data that characterizes relationships between two or more landmarks on one or more of the bones of the joint of the patient (300). For example, surgical assistance system 100 may determine a CSA of the patient and include data indicating the CSA of the patient into the bony landmark data.

Additionally, surgical assistance system 100 (e.g., classification system 118 of surgical assistance system 100) may apply a classifier algorithm that has been trained using training data to select a class associated with the patient from among a plurality of classes (302). The classifier algorithm takes the bony landmark data of the patient as input. As described elsewhere in this disclosure, the classifier algorithm may be one of a neural network algorithm, a support vector machine algorithm, a random forest algorithm, or another type of machine learning algorithm.

The following is a non-limiting list of aspects that are in accordance with one or more techniques of this disclosure.

Aspect 1. A method comprising: generating, by a surgical assistance system and based on medical imaging data of bones of a joint of a patient, bony landmark data that characterizes one or more relationships between two or more landmarks of one or more bones of the bones of the joint of the patient; and applying, by the surgical assistance system, a classifier algorithm that has been trained using training data to select a class associated with the patient from among a plurality of classes, wherein the classifier algorithm takes the bony landmark data of the patient as input.

Aspect 2. The method of aspect 1, wherein the classifier algorithm is one of a neural network algorithm, a support vector machine algorithm, or a random forest algorithm.

Aspect 3. The method of any of aspects 1-2, wherein the joint of the patient is a shoulder joint of the patient, and wherein generating the bony landmark data comprises: determining a critical shoulder angle (CSA) of the patient, wherein the CSA of the patient is an angle between a first line and a second line, the first line being a line between a most superior point on a border of a glenoid cavity of a scapula of the patient and a most inferior point on the border of the glenoid cavity of the scapula of the patient, the second line being a line between the most inferior point on the border of the glenoid cavity of the scapula of the patient and a most lateral point of an acromion of the scapula of the patient; and including data indicating the CSA of the patient into the bony landmark data.

Aspect 4. The method of any of aspects 1-3, wherein the classifier algorithm takes biomechanical model data as input, wherein the biomechanical model data characterizes a biomechanical model of the joint of the patient.

Aspect 5. The method of aspect 4, wherein the biomechanical model data includes data indicating at least one of: static stress of muscles on the bones of the joint, static stress of an orthopedic prosthesis on one or more of the bones of the joint, static stress of two orthopedic prostheses of the joint on each other, dynamic stress of muscles on the bones of the joint, dynamic stress of an orthopedic prosthesis on one or more of the bones of the joint, or dynamic stress of two orthopedic prostheses of the joint on each other.

Aspect 6. The method of any of aspects 1-5, wherein the classifier algorithm takes one or more bone density metrics of a specific bone of the joint as input.

Aspect 7. The method of aspect 6, wherein the specific bone is a humerus and the one or more bone density metrics include a value defined as $(x-z)/z$, wherein x is an inner diameter of the humerus on a plane located a specific distance inferior to a greater tuberosity of the humerus and z is an outer diameter of the humerus on the plane.

Aspect 8. The method of any of aspects 6-7, wherein the specific bone is a humerus and the one or more bone density metrics include a mean of a first value, a second value, a third value, and a fourth value, wherein: the first value is a lateral cortical thicknesses of a humeral diaphysis at a first level, the second value is a medial cortical thickness of the humeral diaphysis at the first level, the third value is a lateral cortical thickness of the humeral diaphysis at a second level, the fourth value is a medial cortical thicknesses of the humeral diaphysis at the second level, and the first level is at a location on the humeral diaphysis where endosteal borders of the lateral and medial cortices of the humerus are first parallel to each other, as determined from a proximal tip of the humerus.

Aspect 9. The method of any of aspects 6-8, wherein a region of the specific bone is partitioned into blocks and the bone density metrics include a value indicating an average of Hounsfield units for the blocks that exceed a threshold.

Aspect 10. The method of aspect 9, wherein the threshold is one of 400, 500, or 700 Hounsfield units.

Aspect 11. The method of any of aspects 9-10, wherein the region is limited to cortical bone of the specific bone.

Aspect 12. The method of any of aspects 9-10, where the region is limited to cancellous bone of the specific bone.

Aspect 13. The method of any of aspects 1-12, wherein the classes correspond to different surgeries for the patient.

Aspect 14. The method of any of aspects 1-13, wherein the classes correspond to different pathologies.

Aspect 15. A computing system comprising: a memory configured to store medical imaging data; and processing circuitry configured to perform the methods of any of aspects 1-14.

Aspect 16. A computing system comprising: means for storing medical imaging data; and means for performing the methods of any of aspects 1-14.

Aspect 17. A computer-readable data storage medium having instructions stored thereon that, when executed, cause a computing system to perform the methods of any of aspects 1-14.

While the techniques been disclosed with respect to a limited number of examples, those skilled in the art, having the benefit of this disclosure, will appreciate numerous modifications and variations there from. For instance, it is contemplated that any reasonable combination of the described examples may be performed. It is intended that the appended claims cover such modifications and variations as fall within the true spirit and scope of the invention.

It is to be recognized that depending on the example, certain acts or events of any of the techniques described herein can be performed in a different sequence, may be added, merged, or left out altogether (e.g., not all described acts or events are necessary for the practice of the techniques). Moreover, in certain examples, acts or events may be performed concurrently, e.g., through multi-threaded processing, interrupt processing, or multiple processors, rather than sequentially.

In one or more examples, the functions described may be implemented in hardware, software, firmware, or any combination thereof. If implemented in software, the functions may be stored on or transmitted over as one or more instructions or code on a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transitory media, but are instead directed to non-transitory, tangible storage media. Disk and disc, as used herein, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Operations described in this disclosure may be performed by one or more processors, which may be implemented as fixed-function processing circuits, programmable circuits, or combinations thereof, such as one or more digital signal processors (DSPs), general purpose microprocessors, application specific integrated circuits (ASICs), field programmable gate arrays (FPGAs), or other equivalent integrated or discrete logic circuitry. Fixed-function circuits refer to circuits that provide particular functionality and are preset on the operations that can be performed. Programmable circuits refer to circuits that can programmed to perform various tasks and provide flexible functionality in the operations that can be performed. For instance, programmable circuits may execute instructions specified by software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable. Accordingly, the terms "processor" and "processing circuitry," as used herein may refer to any of the foregoing structures or any other structure suitable for implementation of the techniques described herein.

Various examples have been described. These and other examples are within the scope of the following claims.

What is claimed is:

1. A method comprising:
generating, by a surgical assistance system and based on medical imaging data of bones of a joint of a patient, bony landmark data that characterizes one or more relationships between two or more landmarks of one or more bones of the bones of the joint of the patient; and
applying, by the surgical assistance system, a classifier algorithm that has been trained using training data to select a class associated with the patient from among a plurality of classes, wherein the classifier algorithm takes the bony landmark data of the patient as input, wherein the classifier algorithm takes biomechanical model data as input, wherein the biomechanical model data characterizes a biomechanical model of the joint of the patient, and wherein the biomechanical model data includes data indicating static stress of muscles on the bones of the joint.

2. The method of claim 1, wherein the classifier algorithm is one of a neural network algorithm, a support vector machine algorithm, or a random forest algorithm.

3. The method of claim 1, wherein the joint of the patient is a shoulder joint of the patient, and wherein generating the bony landmark data comprises:
determining a critical shoulder angle (CSA) of the patient, wherein the CSA of the patient is an angle between a first line and a second line, the first line being a line between a most superior point on a border of a glenoid cavity of a scapula of the patient and a most inferior point on the border of the glenoid cavity of the scapula of the patient, the second line being a line between the most inferior point on the border of the glenoid cavity of the scapula of the patient and a most lateral point of an acromion of the scapula of the patient; and
including data indicating the CSA of the patient into the bony landmark data.

4. The method of claim 1, wherein the classifier algorithm further takes one or more bone density metrics of a specific bone of the joint as input.

5. The method of claim 4, wherein the specific bone is a humerus and the one or more bone density metrics include a value defined as (x−z)/z, wherein x is an inner diameter of the humerus on a plane located a specific distance inferior to a greater tuberosity of the humerus and z is an outer diameter of the humerus on the plane.

6. The method of claim 4, wherein the specific bone is a humerus and the one or more bone density metrics include a mean of a first value, a second value, a third value, and a fourth value, wherein:
the first value is a lateral cortical thicknesses of a humeral diaphysis at a first level, the second value is a medial cortical thickness of the humeral diaphysis at the first level, the third value is a lateral cortical thickness of the humeral diaphysis at a second level, the fourth value is a medial cortical thicknesses of the humeral diaphysis at the second level, and
the first level is at a location on the humeral diaphysis where endosteal borders of lateral and medial cortices of the humerus are parallel to each other, as determined from a proximal tip of the humerus.

7. The method of claim 4, wherein a region of the specific bone is partitioned into blocks and the bone density metrics include a value indicating an average of Hounsfield units for the blocks that exceed a threshold.

8. The method of claim 7, wherein the threshold is one of 400, 500, or 700 Hounsfield units.

9. The method of claim 7, wherein the region is limited to one of: cortical bone of the specific bone or cancellous bone of the specific bone.

10. The method of claim 1, wherein the classes correspond to different surgeries for the patient.

11. The method of claim 1, wherein the classes correspond to different pathologies.

12. A computing system comprising:
one or more memories configured to store medical imaging data; and
processing circuitry configured to:
generate, based on medical imaging data of bones of a joint of a patient, bony landmark data that characterizes one or more relationships between two or more landmarks of one or more bones of the bones of the joint of the patient; and
apply a classifier algorithm that has been trained using training data to select a class associated with the patient from among a plurality of classes, wherein the classifier algorithm takes the bony landmark data of the patient as input, wherein the classifier algorithm takes biomechanical model data as input, wherein the biomechanical model data characterizes a biomechanical model of the joint of the patient, and wherein the biomechanical model data includes data indicating static stress of muscles on the bones of the joint.

13. The computing system of claim 12, wherein the classifier algorithm is one of a neural network algorithm, a support vector machine algorithm, or a random forest algorithm.

14. The computing system of claim 12, wherein the joint of the patient is a shoulder joint of the patient, and wherein the processing circuitry is configured such that, as part of generating the bony landmark data, the processing circuitry:
determines a critical shoulder angle (CSA) of the patient, wherein the CSA of the patient is an angle between a first line and a second line, the first line being a line between a most superior point on a border of a glenoid cavity of a scapula of the patient and a most inferior point on the border of the glenoid cavity of the scapula of the patient, the second line being a line between the most inferior point on the border of the glenoid cavity of the scapula of the patient and a most lateral point of an acromion of the scapula of the patient; and
includes data indicating the CSA of the patient into the bony landmark data.

15. The computing system of claim 12, wherein the classifier algorithm takes one or more bone density metrics of a specific bone of the joint as input.

16. The computing system of claim 15, wherein a region of the specific bone is partitioned into blocks and the bone density metrics include a value indicating an average of Hounsfield units for the blocks that exceed a threshold.

17. The computing system of claim 12, wherein the classes correspond to one of: different surgeries for the patient or different pathologies.

18. One or more non-transitory computer-readable data storage media having instructions stored thereon that, when executed, cause a computing system to:
- generate, based on medical imaging data of bones of a joint of a patient, bony landmark data that characterizes one or more relationships between two or more landmarks of one or more bones of the bones of the joint of the patient; and
- apply a classifier algorithm that has been trained using training data to select a class associated with the patient from among a plurality of classes, wherein the classifier algorithm takes the bony landmark data of the patient as input, wherein the classifier algorithm takes biomechanical model data as input, wherein the biomechanical model data characterizes a biomechanical model of the joint of the patient, and wherein the biomechanical model data includes data indicating static stress of muscles on the bones of the joint.

* * * * *